United States Patent [19]

Böhner et al.

[11] Patent Number: 4,940,482

[45] Date of Patent: Jul. 10, 1990

[54] AMINOPYRAZINONES AND AMINOTRIAZINONES OF THE FORMULA

[75] Inventors: Beat Böhner, Binningen; Willy Meyer, Riehen, both of Switzerland

[73] Assignee: Ciba-Geigy Corporation, Ardsley, N.Y.

[21] Appl. No.: 394,389

[22] Filed: Aug. 15, 1989

Related U.S. Application Data

[60] Continuation-in-part of Ser. No. 260,642, Oct. 21, 1988, abandoned, which is a division of Ser. No. 99,036, Sep. 21, 1987, Pat. No. 4,795,486.

[30] Foreign Application Priority Data

Sep. 26, 1986 [CH] Switzerland ............... 3871/86

[51] Int. Cl.$^5$ .................. A01N 43/60; A01N 43/08; A01N 43/10; C07D 241/18; C07D 253/06
[52] U.S. Cl. ............................... 71/92; 71/90; 71/93; 544/182; 544/405; 544/408
[58] Field of Search ............. 544/405, 408; 71/90, 71/92

[56] References Cited

U.S. PATENT DOCUMENTS

| | | | |
|---|---|---|---|
| 4,419,121 | 12/1983 | Meyer et al. | 71/92 |
| 4,561,878 | 12/1985 | Meyer et al. | 71/92 |
| 4,707,551 | 11/1987 | Böhner et al. | 544/408 |
| 4,802,908 | 2/1989 | Hillermann | 71/70 |

OTHER PUBLICATIONS

Meyer et al., CA 96-217888n (1982).
Meyer et al., CA 102-132065j (1985).
Varkonda et al., CA 104-125062u (1986).

*Primary Examiner*—Cecila Shen
*Attorney, Agent, or Firm*—Kevin T. Mansfield; Edward McC. Roberts

[57] ABSTRACT

Aminopyrazinones and aminotriazinones of the formula

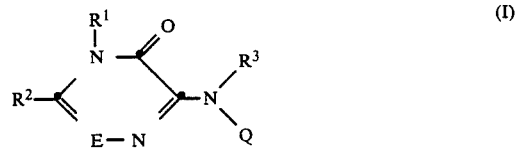

and the salts of these compounds with amines, alkali metal or alkaline earth metal bases or quaternary ammonium bases have good pre- and post-emergent selective herbicidal and growth-regulating properties. In this formula, E is $=CR^4-$, $R^1$ is $C_1-C_4$-alkyl, $R^2$ is $C_1-C_3$-alkyl, $C_1-C_3$-halogenoalkyl, $C_1-C_3$-alkoxy, $C_1-C_3$-halogenoalkoxy, $C_1-C_3$-alkylthio, $C_1-C_3$-alkylsulfinyl, $C_1-C_2$-alkoxyethoxy, $C_1-C_3$-alkylsulfonyl or $-NR^5R^6$, $R^3$ is hydrogen or $C_1-C_3$-alkyl and Q is a group

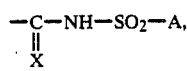

in which $R^4$ is hydrogen, $C_1-C_3$-alkyl, $C_1-C_3$-halogenoalkyl, $C_1-C_3$-alkoxy, cyclopropyl, $C_1-C_3$-halogenoalkoxy, $C_1-C_3$-alkylthio, $C_2-C_4$-alkoxyalkyl, $C_3-C_5$-dialkoxymethyl, halogen or $-NR^5R^6$, $R^5$ and $R^6$ independently of one another are hydrogen or $C_1-C_3$-alkyl, X is oxygen or sulfur and A is a group

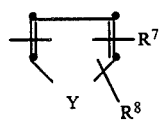

in which Y is oxygen, sulfur, $-CH=CH-$, $-NR^9-$ or $-CR^{10}=N-$, $R^7$ is hydrogen, halogen, $C_1-C_3$-alkyl, $C_1-C_3$-alkoxy, nitro or trifluoromethyl, $R^8$ is hydrogen, halogen, $C_1-C_3$-alkyl, $C_1-C_3$-alkoxy, nitro, $-C\equiv CH$, or one of the groups

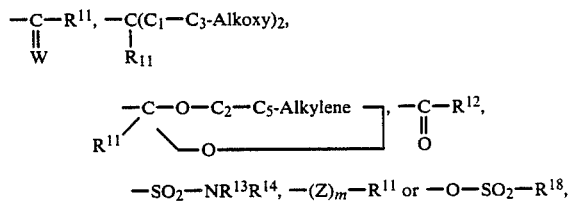

$-SO_2-NR^{13}R^{14}$, $-(Z)_m-R^{11}$ or $-O-SO_2-R^{18}$, $R^9$ and $R^{10}$ independently of one another are hydrogen, $C_1-C_3$-alkyl or $C_2-C_4$-alkenyl, $R^{11}$ is hydrogen, $C_1-C_3$-alkyl, $C_1-C_3$-halogenoalkyl, $C_3-C_6$-cycloalkyl or $C_2-C_4$-alkoxyalkyl, $R^{12}$ is $C_1-C_6$-alkoxy, $C_3-C_6$-alkenyloxy, $C_3-C_6$-alkinyloxy, $C_2-C_6$-halo-genoalkoxy, $C_1-C_4$-cyanoalkoxy, $C_1-C_6$-alkylthio, $C_3-C_6$-alkenylthio, $C_3-C_6$-alkenylthio, $C_5-C_6$-cycloalkoxy, $C_2-C_6$-alkoxyalkoxy or $-NR^{16}R^{17}$, $R^{13}$ is hydrogen, $C_1-C_3$-alkyl or $C_3-C_4$-alkenyl, $R^{14}$ is hydrogens $C_1-C_3$-alkyl, $C_1-C_3$-cyanoalkyl or $C_1-C_3$-alkoxy, $R^{15}$ is $C_3-C_6$-alkinyl, $C_2-C_6$-alkenyl, $C_1-C_6$-alkyl, $C_1-C_4$-halogenoalkyl, $C_2-C_4$-halogenoalkenyl or $C_1-C_4$-alkyl, substituted by cyano, methoxy, ethoxy, nitro, $C_1-C_4$-alkoxycarbonyl, methylthio, ethylthio, methylsulfonyl or ethylsulfonyl; or $C_3-C_4$-alkenyl substituted by nitro, cyano, methoxy or ethoxy, $R^{16}$ is hydrogen, $C_1-C_3$-alkyl or $C_3-C_4$-alkenyl, $R^{17}$ is hydrogen, $C_1-C_3$-alkyl, $C_1-C_3$-cyanoalkyl or $C_1-C_3$-alkoxy, $R^{18}$ is $C_1-C_3$-alkyl and $C_1-C_3$-halogenoalkyl, W is oxygen or sulfur, Z is oxygen, sulfur, $-SO-$ or $-SO_2-$ and m is the number zero or one.

16 Claims, No Drawings

AMINOPYRAZINONES AND AMINOTRIAZINONES OF THE FORMULA

CROSS REFERENCE TO RELATED APPLICATIONS

This is a continuation-in-part of application Ser. No. 260,642 filed on Oct. 21, 1988 now abandoned which in turn is a divisional of application Ser. No. 099,036 filed Sept. 21, 1987, now U.S. Pat. No. 4,795,486.

The present invention relates to novel herbicidally active and plant growth-regulating aminopyrazinones, processes for their preparation, the compositions containing them as active substances and their use for combating weeds, in particular for selectively combating weeds in crops of useful plants, or for regulating and inhibiting plant growth.

The aminopyrazinones according to the invention are those of the formula I

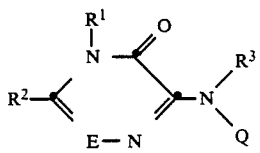

in which E is $=CR^4-$, $R^1$ is $C_1-C_4$-alkyl, $R^2$ is $C_1-C_3$-alkyl, $C_1-C_3$-halogenalkyl, $C_1-C_3$-alkoxy, $C_1-C_3$-halogenalkoxy, $C_1-C_3$-alkylthio, $C_1-C_3$-alkylsulfinyl, $C_1-C_2$-alkoxyethoxy, $C_1-C_3$-alkylsulfonyl or $NR^5R^6$, $R^3$ is hydrogen or $C_1-C_3$-alkyl and Q is a group

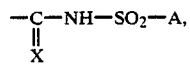

in which $R^4$ is hydrogen, $C_1-C_3$-alkyl, $C_1-C_3$-halogenoalkyl, $C_1-C_3$-alkoxy, cyclopropyl, $C_1-C_3$-halogenoalkoxy, $C_1-C_3$-alkylthio, $C_2-C_4$-alkoxyalkyl, $C_3-C_5$-dialkoxymethyl halogen or $-NR^5R^6$, $R^5$ and $R^6$ independently of one another are hydrogen or $C_1-C_3$-alkyl, X is oxygen or sulfur and A is a group

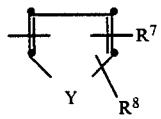

in which Y is oxygen, sulfur, $-CH=CH-$, $-NR^9-$ or $-CR^{10}=N-$, $R^7$ is hydrogen, halogen, $C_1-C_3$-alkyl, $C_1-C_3$-alkoxy, nitro or trifluoromethyl, $R^8$ is hydrogen, halogen, $C_1-C_3$-alkyl, $C_1-C_3$-alkoxy, nitro, $-C\equiv CH$, or one of the groups

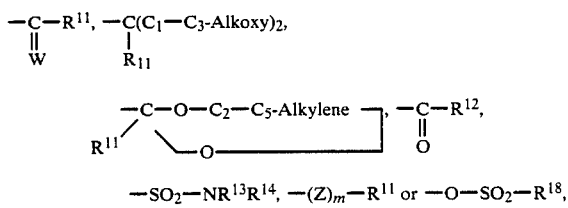

$R^9$ and $R^{10}$ independently of one another are hydrogen, $C_1-C_3$-alkyl or $C_2-C_4$-alkenyl, $R^{11}$ is hydrogen, $C_1-C_3$-alkyl, $C_1-C_3$-halogenoalkyl, $C_3-C_6$-cycloalkyl or $C_2-C_4$-alkoxyalkyl, $R^{12}$ is $C_1-C_6$-alkoxy, $C_3-C_6$-alkenyloxy, $C_3-C_6$-alkinyloxy, $C_2-C_6$-halogenoalkoxy, $C_1-C_4$-cyanoalkoxy, $C_1-C_6$-alkylthio, $C_3-C_6$-alkenylthio, $C_3-C_6$-alkinylthio, $C_5-C_6$-cycloalkoxy, $C_2-C_6$-alkoxyalkoxy or $-NR^{16}R^{17}$, $R^{13}$ is hydrogen, $C_1-C_3$-alkyl or $C_3-C_4$-alkenyl, $R^{14}$ is hydrogen, $C_1-C_3$-alkyl, $C_1-C_3$-cyanoalkyl or $C_1-C_3$-alkoxy, $R^{15}$ is $C_3-C_6$-alkinyl, $C_2-C_6$-alkenyl, $C_1-C_6$-alkyl, $C_1-C_4$-halogenoalkyl, $C_2-C_4$-halogenoalkenyl or $C_1-C_4$-alkyl, substituted by cyano, methoxy, ethoxy, nitro, $C_1-C_4$-alkoxycarbonyl, methylthio, ethylthio, methylsulfonyl or ethylsulfonyl; or $C_3-C_4$-alkenyl substituted by nitro, cyano, methoxy or ethoxy, $R^{16}$ is hydrogen, $C_1-C_3$-alkyl or $C_3-C_4$-alkenyl, $R^{17}$ is hydrogen, $C_1-C_3$-alkyl, $C_1-C_3$-cyanoalkyl or $C_1-C_3$-alkoxy, $R^{18}$ is $C_1-C_3$-alkyl and $C_1-C_3$-halogenoalkyl, W is oxygen or sulfur, Z is oxygen, sulfur, $-SO-$ or $-SO_2-$ and m is the number zero or one, and the salts of these compounds.

Pyrimidine compounds with a herbicidal action are generally known. Such compounds with a herbicidal and plant growth-regulating action have recently been described, for example in Published European Patent Application Nos. 44,807, 44,808 and 126,711.

In the definitions, alkyl is to be understood as meaning straight-chain or branched alkyl; for example: methyl, ethyl, n-propyl, i-propyl or the four isomers of butyl.

Alkoxy is to be understood as meaning: methoxy, ethoxy, n-propyloxy, i-propyloxy or the four isomers of butyloxy but in particular methoxy, ethoxy or i-propyloxy.

Examples of alkylthio are methylthio, ethylthio, n-propylthio, i-propylthio and the four isomers of butylthio, but in particular methylthio and ethylthio.

Halogen itself and as part of a substituent, such as in halogenoalkoxy, halogenoalkylthio or halogenoalkyl, is to be understood as meaning fluorine, chlorine or bromine, but preferably fluorine or chlorine. Halogenoalkyl itself or as part of halogenoalkoxy or halogenoalkylthio is as a rule chloromethyl, fluoromethyl, difluoromethyl, trifluoromethyl, 2-chloroethyl, 2,2,2-trifluoroethyl, 1,1,2,2-tetrafluoroethyl, pentafluoroethyl, 1,1,2-trifluoro-2-chloroethyl, 2,2,2-trifluoro-1,1-dichloroethyl, pentachloroethyl, 3,3,3-trifluoropropyl, 2,3-dichloropropyl or 1,1,2,3,3,3-hexafluoropropyl, but in particular fluoromethyl, chloromethyl, difluoromethyl or trifluoromethyl.

Examples of alkoxyalkyl are: methoxymethyl, methoxyethyl, methoxypropyl, ethoxyethyl, ethoxymethyl and propyloxymethyl. Examples of alkoxyalkoxy are: methoxymethoxy, methoxyethoxy, methoxypropyloxy, ethoxymethoxy, ethoxyethoxy and propyloxymethoxy. Alkylene groups in the context of the definition under formula I are ethylene, propylene, butylene, 1-methylethylene, 1-ethylethylene, 2-methylbutylene or 1-methylbutylene. Dialkoxymethyl is preferably dimethoxymethyl or diethoxymethyl.

The invention also relates to the salts which the compounds of the formula I can form with amines, alkali metal and alkaline earth metal bases or quaternary ammonium bases.

Preferred alkali metal and alkaline earth metal hydroxides as salt-forming agents are the hydroxides of lithium, sodium, potassium, magnesium or calcium, but in particular those of sodium or potassium.

Examples of amines which are suitable for salt formation are primary, secondary and tertiary aliphatic and aromatic amines, such as methylamine, ethylamine, propylamine, i-propylamine, the four isomeric butylamines, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and i-quinoline, but in particular ethyl-, propyl-, diethyl- or triethylamine, and especially iso-propylamine, diethanolamine and 1,4-diazabicyclo[2.2.2]octane.

Examples of quaternary ammonium bases are in general the cations of halogenoammonium salts, for example the tetramethylammonium cation, the tetraethylammonium cation or the trimethylethylammonium cation, or alternatively the ammonium cation.

Preferred compounds of the formula I are those in which either (a) X is oxygen, or (b) A is the group

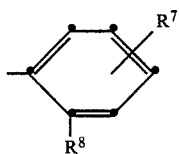

or (c) $R^3$ is hydrogen, or (d) $R^1$ is methyl or ethyl and $R^2$ is methoxy or methyl.

Preferred compounds of group (b) are those in which $R^7$ is hydrogen and $R^8$ is methoxycarbonyl, ethoxycarbonyl, dimethylaminosulfonyl, ethoxy, propoxy, difluoromethoxy, trifluoromethyl, chloroethoxy, methoxyethoxy, 2,2,2-trifluoroethoxy, 1,2-dichlorovinyloxy, nitro, fluorine, chlorine, bromine, methyl, methylthio, difluoromethylthio, chloroethylthio, $-O-SO_2CH_3$, allyloxy or methoxy.

Preferred compounds of group (d) are those in which $R^4$ is chlorine, bromine, methoxy, ethoxy, methyl, ethyl, methylthio, dimethylamino, trifluoromethyl or 2,2,2-trfluoroethoxy.

Particularly preferred sub-groups of compounds of the formula I are formed from those compounds in wnich either $R^1$ is methyl or ethyl, $R^2$ is methoxy or methyl, $R^3$ is hydrogen, X is oxygen, A is the group

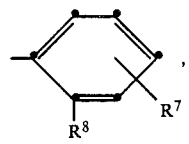

$R^7$ is hydrogen, $R^8$ is methoxycarbonyl, ethoxycarbonyl, dimethylaminosulfonyl, methoxy, ethoxy, diofluoromethoxy, trifluoromethyl, chloroethoxy, methoxyethoxy, 2,2,2-trifluoroethoxy, 1,2-dichlorovinyloxy, nitro, fluorine, chlorine, bromine, methyl, methylthio, difluoromethylthio, chloroethylthio, $-O-SO_2CH_3$ or allyloxy, E is the group $=CR^4-$ and $R^4$ is chlorine, bromine, methoxy, ethoxy, methyl, ethyl, methylthio, dimethylamino, trifluoromethyl or 2,2,2-trifluoroethoxy.

Preferred individual compounds of the formula I which may be mentioned are:

3-[3-(2-methoxycarbonylphenylsulfonyl)-ureido-1,5,6-trimethylpyrazin-2-one and 3-[3-(2-methoxycarbonylphenylsulfonyl)-ureido]-1,6-dimethyl-pyrazin-2-one.

The compounds of the formula I are in general prepared by the following methods.

According to a first process, the compounds of the formula I are obtained by reacting an aminopyrazinone or aminotriazinone of the formula II

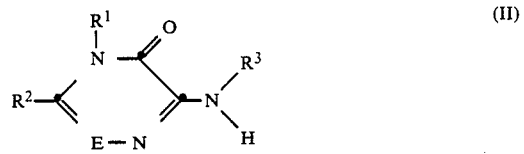

in which $R^1$, $R^2$, $R^3$ and E are as defined under formula I, with a sulfonyl isocyanate of the formula III $$X=C=N-SO_2-A \qquad (III)$$

in which A and X are as defined under formula I.

According to a second process, the compounds of the formula I are obtained by reacting an aminopyrazinone or aminotriazinone of the formula II with a sulfonyl carbamate of the formula IV

in which A and X are as defined under formula I and R is phenyl, alkyl or substituted phenyl, in the presence of a base.

Finally, the compounds of the formula I can also be obtained by reacting a carbamate of the formula V

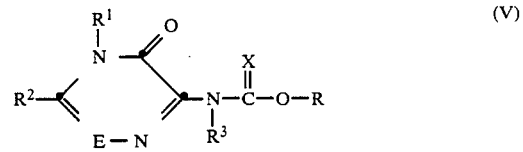

in which $R^1$, $R^2$, $R^3$, E and X are as defined under formula I and R is phenyl, alkyl or substituted phenyl, with a sulfonamide of the formula VI $$H_2N-SO_2-A \qquad (VI)$$

in which A is as defined under formula I, in the presence of a base.

If desired, the resulting ureas of the formula I can be converted into addition salts by means of amines, alkali metal or alkaline earth metal hydroxides or quaternary ammonium bases. This is effected, for example, by reaction with the equimolar amount of a base and evaporation of the solvent.

The reactions to give compounds of the formula I are advantageously carried out in aprotic inert organic solvents. Such solvents are hydrocarbons, such as benzene, toluene, xylene or cyclohexane, carbon tetrachloride, chlorobenzene, ethers, such as diethyl ether, ethylene glycol dimethyl ether, diethylene glycol dimethyl ether, tetrahydrofuran or dioxane, nitriles, such as acetonitrile or propionitrile, or amides, such as dimethylformamide, diethylformamide or N-methylpyrrolidinone. The reaction temperatures are preferably between $-20°$ and $+120°$ C. The reactions of the coupling processes in general proceed as slightly exothermic reactions and can be carried out at room temperature. For the purpose of shortening the reaction time or of initiating the reaction, it is expedient to heat the reaction mixture up to its boiling point for a short time. The reaction times can also be shortened by addition of a few drops of a base as a reaction catalyst. Particularly suitable bases are tertiary amines, such as trimethylamine, triethylamine, quinuclidine, 1,4-diazabicyclo[2.2.2]-octane, 1,5-diazabicyclo[4.3.0]non-5-ene or 1,8-diazabicyclo[5.4.0]undec-7-ene. However, inorganic bases, such as hydrides, such as sodium or calcium hydride, hydroxides, such as sodium and potassium hydroxide, carbonates, such as sodium and potassium carbonate, or bicarbonates, such as potassium and sodium bicarbonate, can also be used as the bases.

The end products of the formula I can be isolated by concentrating the mixture and/or evaporating off the solvent and can be purified by recrystallization or trituration of the solid residue in solvents in which they are not readily soluble, such as ethers, aromatic hydrocarbons or chlorinated hydrocarbons.

The intermediate products of the formulae III, IV and Vi and their preparation are known from the literature. These substances are described, for example, in U.S. Pat. Nos. 4,127,405, 4,305,884, European Pat. No. A-13,480, European Pat. No. A-44,807 and European Pat. No. A-44,808.

The aminopyrazinones of the formula II used as starting materials are known in some cases from the literature. The novel compounds of the formula II have been developed and prepared specifically for the preparation of the active substances according to the invention.

The carbamates of the formula V are obtained from the amino compounds of the formula II by reaction with carbonic acid derivatives of the formula VII

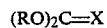

(VII)

in which R and X are as defined above.

The carbonic acid derivatives of the formula VII are known and some of them are commercially available.

The starting materials of the formula II can be prepared by various methods depending on the substitution sought.

The aminopyrazinones of the sub-formula IIB

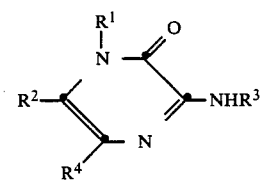

(IIb)

in which $R^1$, $R^2$, $R^3$ and $R^4$ are as defined under formula I, are prepared by reacting a 2-amino-pyrazinone of the formula XI

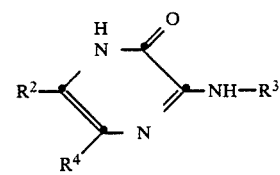

(XI)

in which $R^2$, $R^3$ and $R^4$ are as defined under formula I, with alkylating agents, for example alkyl halides, alkyl tosylates or dialkyl sulfates, in the presence of a base. Alkylations of this type are described, for example, in J. Chem. Soc. 1965, 6681. Starting substances of the formula XI are known or can be obtained by methods analogous to published methods.

Aminopyrazines of the formula IIb are also obtained by reacting pyrazinones of the formula XII

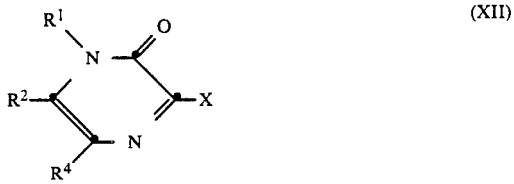

(XII)

in which $R^1$, $R^2$ and $R^4$ are as defined under formula I and X is Cl, Br or $OSO_2CF_3$, with an amine of the formula XIII $$H_2N-R^3$$ (XIII)

in which $R^3$ is hydrogen or $C_1-C_3$-alkyl. Syntheses of this type are described in J. Het. Chem. 20, 919-923 (1983).

Pyrazinones of the sub-formula XIIa

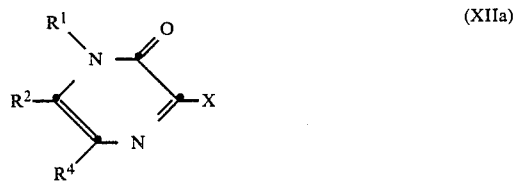

(XIIa)

in which $R^2$ is $C_1-C_4$-alkyl, $R^4$ is $-NR^5R^6$, $C_1-C_3$-alkylthio, $C_1-C_3$-alkoxy or $C_2-C_3$-halogenoalkoxy and $R^1$ and X are as defined in formula XII, are prepared by reacting pyrazinones of the formula XIV

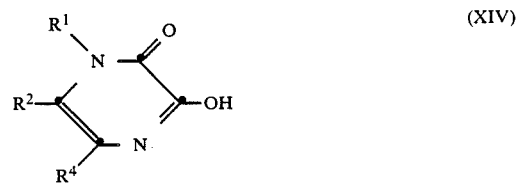

(XIV)

in which $R^1$, $R^2$ and $R^4$ are as defined in formula XIIa, with $(CF_3SO_2)_2O$, $PCl_5$, $POCl_3$, $POBr_3$, $(COCl)_2$ or $(COBr)_2$, if appropriate in the presence of a base, in inert solvents, such as, for example, dichloromethane, acetonitrile, chloroform or carbon tetrachloride.

Pyrazinones of the formula XIV or alkali metal salts thereof are obtained by acylating aminoalkylcyanides of the formula XV

(XV)

in which $R^1$ is $C_1-C_4$-alkyl and $R^2$ is hydrogen or $C_1-C_3$-alkyl, with oxalic acid chlorides of the formula XVI

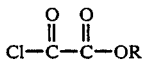 (XVI)

in which R is $C_1$–$C_3$-alkyl, and subsequently reacting the products with nucleophiles of the formula XVII,

 (XVII)

in which $R^4$ is as defined in formula XIIa, if appropriate in the presence of a base.

The pyrazinones of the sub-formula XIIb

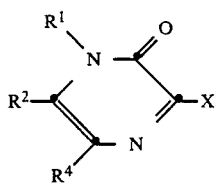 (XIIb)

in which $R^1$ is $C_1$–$C_4$-alkyl, $R^2$ is $C_1$–$C_3$-alkyl and X and $R^4$ are chlorine or bromine, are obtained by reacting aminoalkyl cyanides of the formula XV with oxalyl chloride or bromide.

Syntheses of this type and pyrazinones of the formula XIIb are described in J. Het. Chem. 20, 919–923 (1983).

The pyrazinones of the sub-formula XIIc

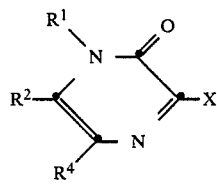 (XIIc)

in which $R^1$, $R^2$ and $R^4$ are as defined in formula I and X is chlorine or bromine, are obtained by reacting pyrazinones of the formula XVIII

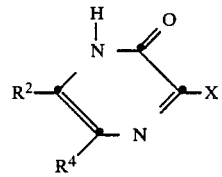 (XVIII)

in which $R^2$, $R^4$ and X are as defined under formula XIIc, with alkylating agents, for example alkyl halides, alkyl tosylates or dialkyl sulfates, in the presence of a base. The starting substances of the formula XVIII are known or can be obtained by methods analogous to published methods.

The active substances of the formula I are stable compounds. Their handling requires no precautionary measures.

When applied in relatively small amounts, the compounds of the formula I are distinguished by good selective growth-inhibiting and selective herbicidal properties, which makes them excellently suitable for use in crops of useful plants, in particular in cereals, rice, cotton, soybean and maize. In some cases, weeds which were previously to be controlled only with total herbicides are also damaged.

The mode of action of these active substances is unusual. Many of them are translocatable, i.e. they are taken up by the plant and transported to other points, where they then act. It is thus possible, for example, to damage perennial weeds down to the roots by surface treatment. In contrast to other herbicides and growth regulators, the novel compounds of the formula I already act when very low amounts are applied.

The compounds of the formula I also have potent plant growth-regulating, in particular plant growth-inhibiting, properties. The growth of both monocotyledons and dicotyledons is impaired.

Thus, for example, the growth of leguminosae frequently planted as cover crops in agriculture in tropical regions can be selectively inhibited by the compounds of the formula I, so that although soil erosion between the crop plants is prevented, the cover crops cannot become competition for the crop.

For many crop plants, an inhibition of vegetative growth allows denser planting of the crop, so that an increased harvest, based on the soil surface, can be achieved.

Another mechanism of increasing yield with growth inhibitors is based on the fact that the nutrients benefit blossom and fruit formation to a greater degree, whilst vegetative growth is restricted.

When larger amounts of active substances of the formula I are applied, the development of all the plants tested is damaged to the extent that they die.

The invention also relates to herbicidal and plant growth-regulating compositions which contain a novel active substance of the formula I, and to processes for pre- and post-emergence weed control and for inhibition of the growth of monocotyledon and dicotyledon plants, in particular grasses, tropical cover crops and tobacco side shoots.

The compounds of the formula I are used in nonmodified form or, preferably, as compositions together with the auxiliaries customary in formulation technology, and are therefore processed in a known manner to emulsion concentrates, directly sprayable or dilutable solutions, diluted emulsions, wettable powders, soluble powders, dusts, granules or encapsulations in, for example, polymeric substances. The methods of use, such as spraying, misting, dusting, scattering or watering, like the nature of the agent, are chosen according to the intended aims and the given circumstances.

The formulations, i.e. the compositions, formulations or combinations containing the active substance of the formula I and if appropriate a solid or liquid additive are prepared in a known manner, for example by intimate mixing and/or grinding of the active substances with extenders, for example with solvents, solid carriers and if appropriate surface-active compounds (surfactants).

Possible solvents are: aromatic hydrocarbons, preferably $C_8$ to $C_{12}$ fractions, for example xylene mixtures or substituted naphthalenes, phthalic acid esters, such as dibutyl or dioctyl phthalate, aliphatic hydrocarbons, such as cyclohexane or paraffins, alcohols and glycols and ethers and esters thereof, such as ethanol, ethylene glycol or ethylene glycol monomethyl or monoethyl ether, ketones, such as cyclohexanone, highly polar solvents, such as N-methyl-2-pyrrolidone, dimethylsulfoxide or dimethylformamide, and if appropriate epoxidized vegetable oils, such as epoxidized coconut oil or soybean oil; or water.

The solid carriers used, for example for dusts and dispersible powders, are as a rule natural rock powders, such as calcite, talc, kaolin, montmorillonite or attapulgite. Highly disperse silicic acid or highly disperse absorbent polymers can also be added to improve the physical properties. Possible granular adsorptive granule carriers are porous types, for example pumice, crushed brick, sepiolite or bentonite, and possible non-adsorptive carrier materials are, for example, calite or sand. A large number of pre-granulated materials of inorganic or organic nature, such as, in particular, dolomite or comminuted plant residues, can moreover be used.

Possible surface-active compounds are, depending on the nature of the active substance of the formula I to be formulated, nonionic, cationic and/or anionic surfactants with good emulsifying, dispersing and wetting properties. Surfactants are also to be understood as meaning surfactant mixtures.

Suitable anionic surfactants can be either so-called water-soluble soaps or water-soluble synthetic surface-active compounds.

Soaps which may be mentioned are the alkali metal, alkaline earth metal or substituted or unsubstituted ammonium salts of higher fatty acids ($C_{10}$–$C_{22}$), for example the Na or K salts of oleic or stearic acid, or of naturally occurring fatty acid mixtures which can be obtained, for example, from coconut oil or tallow oil. Fatty acid methyl-taurine salts may furthermore also be mentioned.

However, so-called synthetic surfactants, in particular fatty sulfonates, fatty sulfates, sulfonated benzimidazole derivatives or alkylarylsulfonates, are more frequently used.

The fatty sulfates or sulfonates are as a rule in the form of alkali metal, alkaline earth metal or substituted or unsubstituted ammonium salts and have an alkyl radical having 8 to 22 C atoms, alkyl also including the alkyl part of acyl radicals, for example the Na or Ca salt of the ligninsulfonic acid, of dodecylsulfuric acid ester or of a fatty alcohol-sulfate mixture prepared from naturally occurring fatty acids. The salts of sulfuric acid esters and sulfonic acids of fatty alcohol-ethylene oxide adducts are also included here. The sulfonated benzimidazole derivatives preferably contain 2-sulfonic acid groups and a fatty acid radical having 8 to 22 C atoms. Alkylarylsulfonates are, for example, the Na, Ca or triethanolamine salts of dodecylbenzenesulfonic acid, of dibutylnaphthalenesulfonic acid or of a naphthalenesulfonic acid-formaldehyde condensation product.

Corresponding phosphates, for example the salts of the phosphoric acid ester of a p-nonylphenol-(4-14)-ethylene, oxide adduct or phospholipids, are furthermore also suitable.

Possible nonionic surfactants are in particular polyglycol ether derivatives of aliphatic or cycloaliphatic alcohols, saturated or unsaturated fatty acids and alkylphenols, which can contain 3 to 10 glycol ether groups and 8 to 20 carbon atoms in the (aliphatic) hydrocarbon radical and 6 to 18 carbon atoms in the alkyl radical of the alkylphenols.

Other suitable nonionic surfactants are the water-soluble adducts, containing 20 to 250 ethylene glycol ether groups and 10 to 100 propylene glycol ether groups, of polyethylene oxide on polypropylene glycol, ethylenediaminopolypropylene glycol and alkylpolypropylene glycol having 1 to 10 carbon atoms in the alkyl chain, the compounds mentioned usually containing 1 to 5 ethylene glycol units per propylene glycol unit.

Examples which may be mentioned of nonionic surfactants are nonylphenolpolyethoxyethanols, castor oil polyglycol ethers, polypropylene-polyethylene oxide adducts, tributylphenoxypolyethoxyethanol, polyethylene glycol and octylphenoxypolyethoxyethanol.

Fatty acid esters of polyoxyethylene sorbitan, such as polyoxyethylene sorbitan trioleate, are furthermore also possible.

The cationic surfactants are in particular quaternary ammonium salts which contain at least one alkyl radical with 8 to 22 C atoms as the N substituent and lower free or halogenated alkyl, benzyl or lower hydroxyalkyl radicals as further substituents. The salts are preferably in the form of halides, methylsulfates or ethylsulfates, for example stearyltrimethylammonium chloride or benzyldi(2-chloroethyl)-ethylammonium bromide.

Surfactants which are customary in formulation technology are described, inter alia, in the following publications: "McCutcheon's Detergents and Emulsifiers Annual" MC Publishing Corp., Ridgewood, N.J., 1981; H. Stache, "Tensid-Taschenbuch (Surfactant handbook)", 2nd edition, C. Hanser Verlag, Munich, Vienna, 1981; and M. and J. Ash. "Encyclopedia of Surfactants", volume I-III, Chemical Publishing Co., New York, 1980–1981.

The agrochemical formulations as a rule contain 0.1 to 95%, in particular 0.1 to 80%, of active substance of the formula I, 1 to 99.9% of a solid or liquid additive and 0 to 25%, in particular 0.1 to 25%, of a surfactant.

Preferred formulations have, in particular, the following compositions: (%=percent by weight).

Emulsifiable concentrates

| Active substance: | 1 to 20%, preferably | 5 to 10% |
|---|---|---|
| Surface-active agent: | 5 to 30%, preferably | 10 to 20% |
| Liquid carrier: | 50 to 94%, preferably | 70 to 85% |

Dusts

| Active substance: | 0.1 to 10%, preferably | 0.1 to 1% |
|---|---|---|
| Solid carrier: | 99.9 to 90%, preferably | 99.9 to 99% |

Suspension concentrates

| Active substance: | 5 to 75%, preferably | 10 to 50% |
|---|---|---|
| Water: | 94 to 24%, preferably | 88 to 30% |
| Surface-active agent: | 1 to 40%, preferably | 2 to 30% |

Wettable powder

| Active substance: | 0.5 to 90%, preferably | 1 to 80% |
|---|---|---|
| Surface-active agent: | 0.5 to 20%, preferably | 1 to 15% |
| Solid carrier: | 5 to 95%, preferably | 15 to 90% |

Granules

| Active substance: | 0.5 to 30%, preferably | 3 to 15% |
|---|---|---|
| Solid carrier: | 99.5 to 70%, preferably | 97 to 85%. |

Whilst concentrated compositions are preferred rather as commercial groups, the end user as a rule uses dilute compositions. The use forms can be diluted down to 0.001% of active substance. The amounts applied are as a rule 0.01 to 10 kg of active substance/ha, preferably 0.025 to 5 kg of active substance/ha.

The compositions can also contain further additives, such as stabilizers, foam suppressants, viscosity regulators, binders, tackifiers and fertilizers or other active substances, in order to achieve special effects.

PREPARATION EXAMPLES

EXAMPLE H1

3-Amino-1,6-dimethylpyrazin-2-one (Compound 7.02)

8.87 g of dimethyl sulfate are added dropwise to a mixture of 8.13 g of 3-amino-6-methylpyrazin-2-one and 72 ml of 1N sodium hydroxide solution at room temperature. After the mixture has been stirred at 20°–25° C. for 15 hours, the precipitate is filtered off, the filtrate is concentrated to one quarter of the volume and the concentrate is extracted with ethyl acetate. 1.7 g of 3-amino-1,6-dimethylpyrazin-2-one with a melting point of 217°–219° C. are obtained by washing with saturated sodium chloride solution, drying with sodium sulfate and concentrating the organic phase.

EXAMPLE H2

3-[3-(2-Methoxycarbonylphenylsulfonyl)-ureido]-1,6-dimethylpyrazin-2-one (Compound 1.02)

A mixture of 1.218 g of 2-methoxycarbonylphenylsulfonyl isocyanate, 0.7 g of 3-amino-1,6-dimethylpyrazin-2-one and 15 ml of absolute dioxane is refluxed for 3 hours. The reaction mixture is evaporated to dryness and the residue is crystallized by treatment with acetone. 0.9 g of 3-[3-(2-methoxycarbonylphenylsulfonyl)-ureido]-1,6-dimethylpyrazin-2-one with a melting point of 192°–193° C. are thus obtained.

TABLE 1

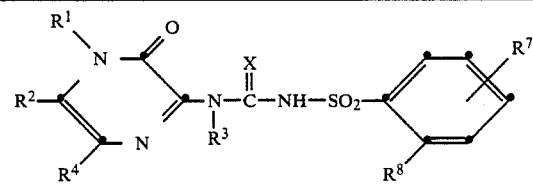

| Compound No. | $R^1$ | $R^2$ | $R^3$ | $R^4$ | $R^7$ | $R^8$ | X | Melting point [°C.] |
|---|---|---|---|---|---|---|---|---|
| 1.01 | $CH_3$ | $CH_3$ | H | $CH_3$ | H | $COOCH_3$ | O | 198–199 |
| 1.02 | $CH_3$ | $CH_3$ | H | H | H | $COOCH_3$ | O | 192–193 |
| 1.03 | $CH_3$ | $CH_3$ | H | Cl | H | $COOCH_3$ | O | |
| 1.04 | $CH_3$ | $CH_3$ | H | $OCH_3$ | H | $COOCH_3$ | O | |
| 1.05 | $C_2H_5$ | $CH_3$ | H | $CH_3$ | H | $COOCH_3$ | O | |
| 1.06 | $C_2H_5$ | $CH_3$ | H | H | H | $COOCH_3$ | O | |
| 1.07 | $C_2H_5$ | $CH_3$ | H | Cl | H | $COOCH_3$ | O | |
| 1.08 | $C_2H_5$ | $CH_3$ | H | $OCH_3$ | H | $COOCH_3$ | O | |
| 1.09 | $CH_3$ | $CH_3$ | H | $CH_3$ | H | $-SO_2N(CH_3)_2$ | O | |
| 1.10 | $CH_3$ | $CH_3$ | H | H | H | $-SO_2N(CH_3)_2$ | O | |
| 1.11 | $CH_3$ | $CH_3$ | H | Cl | H | $-SO_2N(CH_3)_2$ | O | |
| 1.12 | $CH_3$ | $CH_3$ | H | $OCH_3$ | H | $-SO_2N(CH_3)_2$ | O | |
| 1.13 | $C_2H_5$ | $CH_3$ | H | $CH_3$ | H | $-SO_2N(CH_3)_2$ | O | |
| 1.14 | $C_2H_5$ | $CH_3$ | H | H | H | $-SO_2N(CH_3)_2$ | O | |
| 1.15 | $C_2H_5$ | $CH_3$ | H | Cl | H | $-SO_2N(CH_3)_2$ | O | |
| 1.16 | $C_2H_5$ | $CH_3$ | H | $OCH_3$ | H | $-SO_2N(CH_3)_2$ | O | |
| 1.17 | $CH_3$ | $CH_3$ | H | $CH_3$ | H | $OC_2H_5$ | O | |
| 1.18 | $CH_3$ | $CH_3$ | H | H | H | $OC_2H_5$ | O | |
| 1.19 | $CH_3$ | $CH_3$ | H | Cl | H | $OC_2H_5$ | O | |
| 1.20 | $CH_3$ | $CH_3$ | H | $OCH_3$ | H | $OC_2H_5$ | O | |
| 1.21 | $C_2H_5$ | $CH_3$ | H | $CH_3$ | H | $OC_2H_5$ | O | |
| 1.22 | $C_2H_5$ | $CH_3$ | H | H | H | $OC_2H_5$ | O | |
| 1.23 | $C_2H_5$ | $CH_3$ | H | Cl | H | $OC_2H_5$ | O | |
| 1.24 | $C_2H_5$ | $CH_3$ | H | $OCH_3$ | H | $OC_2H_5$ | O | |
| 1.25 | $CH_3$ | $CH_3$ | H | $CH_3$ | H | $OCHF_2$ | O | |
| 1.26 | $CH_3$ | $CH_3$ | H | H | H | $OCHF_2$ | O | |
| 1.27 | $CH_3$ | $CH_3$ | H | Cl | H | $OCHF_2$ | O | |
| 1.28 | $CH_3$ | $CH_3$ | H | $OCH_3$ | H | $OCHF_2$ | O | |
| 1.29 | $C_2H_5$ | $CH_3$ | H | $CH_3$ | H | $OCHF_2$ | O | |
| 1.30 | $C_2H_5$ | $CH_3$ | H | H | H | $OCHF_2$ | O | |
| 1.31 | $C_2H_5$ | $CH_3$ | H | Cl | H | $OCHF_2$ | O | |
| 1.32 | $C_2H_5$ | $CH_3$ | H | $OCH_3$ | H | $OCHF_2$ | O | |
| 1.33 | $CH_3$ | $CH_3$ | H | $CH_3$ | H | $CF_3$ | O | |
| 1.34 | $CH_3$ | $CH_3$ | H | H | H | $CF_3$ | O | |
| 1.35 | $CH_3$ | $CH_3$ | H | Cl | H | $CF_3$ | O | |
| 1.36 | $CH_3$ | $CH_3$ | H | $OCH_3$ | H | $CF_3$ | O | |
| 1.37 | $CH_3$ | $OCH_3$ | H | H | H | $-COOCH_3$ | O | |
| 1.38 | $CH_3$ | $OCH_3$ | H | H | H | $-OCHF_2$ | O | |
| 1.39 | $CH_3$ | $OCH_3$ | H | Br | H | $-COOCH_3$ | O | |
| 1.40 | $CH_3$ | $C_2H_5$ | H | H | H | $-COOCH_3$ | O | |
| 1.41 | $CH_3$ | $C_3H_7$ | H | H | H | $-COOCH_3$ | O | |
| 1.42 | $CH_3$ | $OC_2H_5$ | H | H | H | $-COOCH_3$ | O | |
| 1.43 | $CH_3$ | $SCH_3$ | H | H | H | $-COOCH_3$ | O | |
| 1.44 | $CH_3$ | $N(CH_3)_2$ | H | H | H | $-COOCH_3$ | O | |

TABLE 2

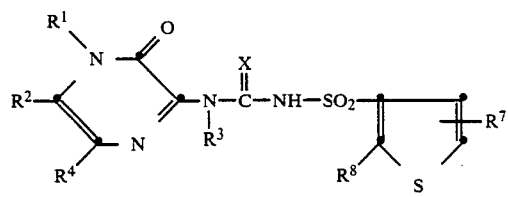

| Compound No. | R$^1$ | R$^2$ | R$^3$ | R$^4$ | R$^7$ | R$^8$ | X | Melting point [°C.] |
|---|---|---|---|---|---|---|---|---|
| 2.01 | CH$_3$ | CH$_3$ | H | CH$_3$ | H | COOCH$_3$ | O | |
| 2.02 | CH$_3$ | CH$_3$ | H | H | H | COOCH$_3$ | O | |
| 2.03 | CH$_3$ | CH$_3$ | H | Cl | H | COOCH$_3$ | O | |
| 2.04 | CH$_3$ | CH$_3$ | H | OCH$_3$ | H | COOCH$_3$ | O | |
| 2.05 | C$_2$H$_5$ | CH$_3$ | H | CH$_3$ | H | COOCH$_3$ | O | |
| 2.06 | C$_2$H$_5$ | CH$_3$ | H | H | H | COOCH$_3$ | O | |
| 2.07 | C$_2$H$_5$ | CH$_3$ | H | Cl | H | COOCH$_3$ | O | |
| 2.08 | C$_2$H$_5$ | CH$_3$ | H | OCH$_3$ | H | COOCH$_3$ | O | |

TABLE 3

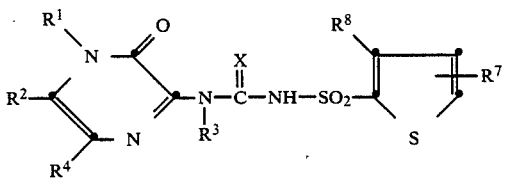

| Compound No. | R$^1$ | R$^2$ | R$^3$ | R$^4$ | R$^7$ | R$^8$ | X | Melting point [°C.] |
|---|---|---|---|---|---|---|---|---|
| 3.01 | CH$_3$ | CH$_3$ | H | CH$_3$ | H | COOCH$_3$ | O | |
| 3.02 | CH$_3$ | CH$_3$ | H | H | H | COOCH$_3$ | O | |
| 3.03 | CH$_3$ | CH$_3$ | H | Cl | H | COOCH$_3$ | O | |
| 3.04 | CH$_3$ | CH$_3$ | H | OCH$_3$ | H | COOCH$_3$ | O | |
| 3.05 | C$_2$H$_5$ | CH$_3$ | H | CH$_3$ | H | COOCH$_3$ | O | |
| 3.06 | C$_2$H$_5$ | CH$_3$ | H | H | H | COOCH$_3$ | O | |
| 3.07 | C$_2$H$_5$ | CH$_3$ | H | Cl | H | COOCH$_3$ | O | |
| 3.08 | C$_2$H$_5$ | CH$_3$ | H | OCH$_3$ | H | COOCH$_3$ | O | |

TABLE 4

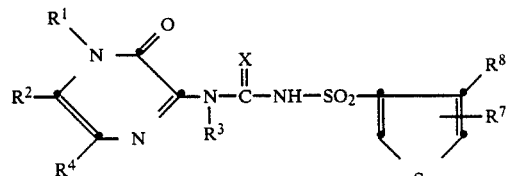

| Compound No. | R$^1$ | R$^2$ | R$^3$ | R$^4$ | R$^7$ | R$^8$ | X | Melting point [°C.] |
|---|---|---|---|---|---|---|---|---|
| 4.01 | CH$_3$ | CH$_3$ | H | CH$_3$ | H | COOCH$_3$ | O | |
| 4.02 | CH$_3$ | CH$_3$ | H | H | H | COOCH$_3$ | O | |
| 4.03 | CH$_3$ | CH$_3$ | H | Cl | H | COOCH$_3$ | O | |
| 4.04 | CH$_3$ | CH$_3$ | H | OCH$_3$ | H | COOCH$_3$ | O | |
| 4.05 | C$_2$H$_5$ | CH$_3$ | H | CH$_3$ | H | COOCH$_3$ | O | |
| 4.06 | C$_2$H$_5$ | CH$_3$ | H | H | H | COOCH$_3$ | O | |
| 4.07 | C$_2$H$_5$ | CH$_3$ | H | Cl | H | COOCH$_3$ | O | |
| 4.08 | C$_2$H$_5$ | CH$_3$ | H | OCH$_3$ | H | COOCH$_3$ | O | |

TABLE 5

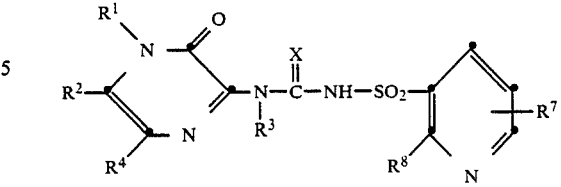

| Compound No. | R$^1$ | R$^2$ | R$^3$ | R$^4$ | R$^7$ | R$^8$ | X | Melting point [°C.] |
|---|---|---|---|---|---|---|---|---|
| 5.01 | CH$_3$ | CH$_3$ | H | CH$_3$ | H | Cl | O | |
| 5.02 | CH$_3$ | CH$_3$ | H | H | H | Cl | O | |
| 5.03 | CH$_3$ | CH$_3$ | H | Cl | H | Cl | O | |
| 5.04 | CH$_3$ | CH$_3$ | H | OCH$_3$ | H | Cl | O | |
| 5.05 | C$_2$H$_5$ | CH$_3$ | H | CH$_3$ | H | Cl | O | |
| 5.06 | C$_2$H$_5$ | CH$_3$ | H | H | H | Cl | O | |
| 5.07 | C$_2$H$_5$ | CH$_3$ | H | Cl | H | Cl | O | |
| 5.08 | C$_2$H$_5$ | CH$_3$ | H | OCH$_3$ | H | Cl | O | |

TABLE 6

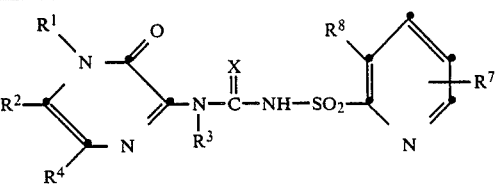

| Compound No. | R$^1$ | R$^2$ | R$^3$ | R$^4$ | R$^7$ | R$^8$ | X | Melting point [°C.] |
|---|---|---|---|---|---|---|---|---|
| 6.01 | CH$_3$ | CH$_3$ | H | CH$_3$ | H | Cl | O | |
| 6.02 | CH$_3$ | CH$_3$ | H | H | H | Cl | O | |
| 6.03 | CH$_3$ | CH$_3$ | H | Cl | H | Cl | O | |
| 6.04 | CH$_3$ | CH$_3$ | H | OCH$_3$ | H | Cl | O | |
| 6.05 | C$_2$H$_5$ | CH$_3$ | H | CH$_3$ | H | Cl | O | |
| 6.06 | C$_2$H$_5$ | CH$_3$ | H | H | H | Cl | O | |
| 6.07 | C$_2$H$_5$ | CH$_3$ | H | Cl | H | Cl | O | |
| 6.08 | C$_2$H$_5$ | CH$_3$ | H | OCH$_3$ | H | Cl | O | |

TABLE 7

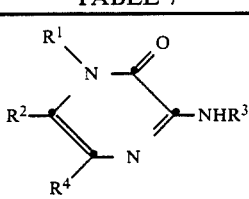

| Compound No. | R$^1$ | R$^2$ | R$^3$ | R$^4$ | Melting point [°C.] |
|---|---|---|---|---|---|
| 7.01 | CH$_3$ | CH$_3$ | H | CH$_3$ | |
| 7.02 | CH$_3$ | CH$_3$ | H | H | 217-219 |
| 7.03 | CH$_3$ | CH$_3$ | H | Cl | |
| 7.04 | CH$_3$ | CH$_3$ | H | OCH$_3$ | |
| 7.05 | C$_2$H$_5$ | CH$_3$ | H | CH$_3$ | |
| 7.06 | C$_2$H$_5$ | CH$_3$ | H | H | |
| 7.07 | C$_2$H$_5$ | CH$_3$ | H | Cl | |
| 7.08 | C$_2$H$_5$ | CH$_3$ | H | OCH$_3$ | |
| 7.09 | CH$_3$ | OCH$_3$ | H | H | |
| 7.10 | C$_2$H$_5$ | OCH$_3$ | H | H | |
| 7.11 | CH$_3$ | OC$_2$H$_5$ | H | H | |
| 7.12 | CH$_3$ | SCH$_3$ | H | H | |
| 7.13 | CH$_3$ | N(CH$_3$)$_2$ | H | H | |
| 7.14 | CH$_3$ | OCH$_3$ | H | Br | |
| 7.15 | CH$_3$ | OCH$_3$ | H | Cl | |

FORMULATION EXAMPLES

EXAMPLE F1

Formulation examples for active substances of the formula I (% = percent by weight)

| (a) Wettable powder | (a) | (b) | (c) |
|---|---|---|---|
| Active substance No. 1.01 | 20% | 50% | 0.5% |
| Na ligninsulfonate | 5% | 5% | 5% |
| Na laurylsulfate | 3% | — | — |
| Na diisobutylnaphthalenesulfonate | — | 6% | 6% |
| Octylphenolpolyethylene glycol ether(7–8 mol of EO) | — | 2% | 2% |
| Highly disperse silicic acid | 5% | 27% | 27% |
| Kaolin | 67% | — | — |
| Sodium chloride | — | — | 59.5% |

The active substance is mixed thoroughly with the additives and the mixture is ground thoroughly in a suitable mill. Wettable powders which can be diluted with water to give suspensions of any desired concentration are obtained.

| (b) Emulsion concentrate | (a) | (b) |
|---|---|---|
| Active substance No. 1.01 | 10% | 1% |
| Octylphenolpolyethylene glycol ether (4–5 mol of EO) | 3% | 3% |
| Ca dodecylbenzenesulfonate | 3% | 3% |
| Castor oil polyglycol ether (36 mol of EO) | 4% | 4% |
| Cyclohexanone | 30% | 10% |
| Xylene mixture | 50% | 79% |

Emulsions of any desired concentration can be prepared from this concentrate by dilution with water.

| (c) Dust | (a) | (b) |
|---|---|---|
| Active substance No. 1.01 | 0.1% | 1% |
| Talc | 99.9% | — |
| Kaolin | — | 99% |

Ready-to-use dusts are obtained by mixing the active substance with the carrier and grinding the mixture on a suitable mill.

| (d) Extruder granules | (a) | (b) |
|---|---|---|
| Active substance No. 1.05 | 10% | 1% |
| Na ligninsulfonate | 2% | 2% |
| Carboxymethylcellulose | 1% | 1% |
| Kaolin | 87% | 96% |

The active substance is mixed with the additives and the mixture is ground and moistened with water. This mixture is extruded and then dried in a stream of air.

| (e) Coated granules | |
|---|---|
| Active substance No. 1.03 | 3% |
| Polyethylene glycol (molecular weight 200) | 3% |
| Kaolin | 94% |

The finely ground active substance is uniformly applied to the kaolin moistened with polyethylene glycol in a mixer. Dust-free coated granules are obtained in this manner.

| (f) Suspension concentrate | (a) | (b) |
|---|---|---|
| Active substance No. 1.01 | 40% | 5% |
| Ethylene glycol | 10% | 10% |
| Nonylphenolpolyethylene glycol ether (15 mol of EO) | 6% | 1% |
| Na ligninsulfonate | 10% | 5% |
| Carboxymethylcellulose | 1% | 1% |
| 37% aqueous formaldehyde solution | 0.2% | 0.2% |
| Silicone oil in the form of a 75% aqueous emulsion | 0.8% | 0.8% |
| Water | 32% | 77% |

The finely ground active substance is intimately mixed with the additives. A suspension concentrate is thus obtained, from which suspensions of any desired concentration can be prepared by dilution with water.

| (g) Salt solution | |
|---|---|
| Active substance No. 1.29 | 5% |
| Isopropylamine | 1% |
| Octylphenolpolyethylene glycol ether (78 mol of EO) | 3% |
| Water | 91% |

BIOLOGICAL EXAMPLES

EXAMPLE B1

Herbicidal action before emergence of the plants

Plastic pots are filled with expanded vermiculite (density: 0.135 g/cm$^3$, water absorption capacity: 0.565 l/l). After the non-adsorptive vermiculite has been saturated with an aqueous emulsion of the active substance in deionized water, which contains the active substances in a concentration of 70.8 ppm, seeds of the following plants are sown on the surface: *Nasturtium officinalis, Agrostis tenuis, Stellaria media* and *Digitaria sanguinalis*. The experimental containers are then kept in a climatically controlled chamber at 20° C. under an illumination of about 20 kLux and a relative-atmospheric humidity of 70%. During a germination phase of 4 to 5 days, the pots are covered with material which is transparent to light in order to increase the local atmospheric humidity and are watered with deionized water. After the 5th day, 0.5% of a commercially available liquid fertilizer (®Greenzit, from Ciba-Geigy) is added to the water used for watering. 12 days after sowing, the experiment is evaluated and the action on the experimental plants is evaluated according to the following scale:

1: plants have not germinated or have completely died
2–3: very potent action
4–6: moderate action
7–8: weak action
9: no action (as untreated control).

PRE-EMERGENT ACTION

Concentration of the active substance emulsion: 70.8 ppm

| Test plant Active substance No. | Nasturtium | Stellaria | Agrostis | Digitaria |
|---|---|---|---|---|
| 1.01 | 2 | 2 | 2 | 2 |

| Test plant Active substance No. | Nasturtium | Stellaria | Agrostis | Digitaria |
|---|---|---|---|---|
| 1.02 | 2 | 3 | 2 | 3 |

EXAMPLE B2

Inhibition of growth of tropical Leguminosae cover crops

The experimental plants (*Centrosema plumieri* and *Centrosema pubescens*) are grown to the fully developed stage and cut back to a height of 60 cm. After 7 days, they are sprayed with the active substance as an aqueous emulsion. The experimental plants are kept at 70% relative atmospheric humidity under 600 lux of artificial light for 14 hours per day at temperatures of 27° during the day and 21° C. during the night. 4 weeks after the application, the experiment is evaluated. The new additional growth is estimated and weighed in comparison with the control and the phytotoxicity is evaluated. In this experiment, the plants treated with the active substances of the formula I show a clear reduction in new additional growth (less than 20% of the new additional growth of untreated crop plants), without the experimental plants thereby being damaged.

EXAMPLE B3

Growth regulation in soyabean

Soybeans of the "Hark" variety are sown in plastic containers with a soil-peat-sand mixture in a ratio of 6:3:1 and the containers are placed in a climatically controlled chamber. By optimum choice of temperature, illumination, addition of fertilizer and watering, the plants develop to the 5-6 trefoil leafe stage after about 5 weeks. At this point in time, the plants are sprayed with an aqueous liquor of an active substance of the formula I and are wetted thoroughly. The active substance concentration is up to 100 g of active substance/ha. Evaluation is carried out about 5 weeks after application of the active substance. In comparison with untreated control plants, the active substances of the formula I according to the invention cause a notable increase in the number and weight of pods on the main shoot.

EXAMPLE B4

Inhibition of growth in cereals

The cereal varieties Hordeum vulgare (spring barley) and Secale (spring rye) are sown in plastic pots with sterilized soil in a greenhouse and are watered as required. About 21 days after sowing, the shoots are sprayed with an aqueous spray liquor of an active substance of the formula I. The amount of active substance is up to 100 g of active substance per hectare. The growth of the cereal is evaluated 21 days after the application. The treated plants show a reduction in new additional growth in comparison with the untreated controls (60-90% of the control), and in some cases an increase in stem diameter.

EXAMPLE B5

Inhibition of growth in grasses

The grasses *Lolium perenne, Poa pratensis, Festuca ovina, Dactylis glomerate* and *Cynodon dactylon* are sown in plastic dishes with a soil-peat-sand mixture (6:3:1) in a greenhouse and are watered as required. The emerged grasses are cut back weekly to a height of 4 cm and about 50 days after sowing and one day after the last cut are sprayed with an aqueous spray liquor of an active substance of the formula I. The amount of active substance, when converted, is up to 100 g of active substance per hectare. 21 days after the administration, the growth of the grasses is evaluated.

The compounds of the formula I effect a reduction in new additional growth of about 10-30% in comparison with the untreated control.

What is claimed is:

1. An aminopyrazinone of the formula I

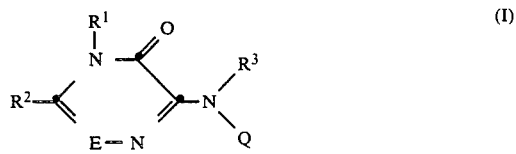

in which E is $=CR^4-$, $R^1$ is $C_1-C_4$-alkyl, $R^2$ is $C_1-C_3$-alkyl, $C_1-C_3$-halogenalkyl, $C_1-C_3$-alkoxy, C $-C_1$-halogenoalkoxy, $C_1-C_3$-alkylthio, $C_1-C_3$-alkylsulfinyl, $C_1-C_2$-alkoxyethoxy, $C_1-C_3$-alkylsulfonyl or $-NR^5R^6$, $R^3$ is hydrogen or $C_1-C_3$-alkyl and Q is a group

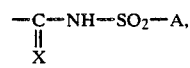

in which $R^4$ is hydrogen, $C_1-C_3$-alkyl, $C_1-C_3$-halogenoalkyl, $C_1-C_3$-alkoxy, cyclopropyl, $C_1-C_3$-halogenoalkoxy, $C_1-C_3$-alkylthio, $C_2-C_4$-alkoxyalkyl, $C_3-C_5$-dialkoxymethyl, halogen or $-NR^5R^6$, $R^5$ and $R^6$ independently of one another are hydrogen or $C_1-C_3$-alkyl, X is oxygen or sulfur and A is a group

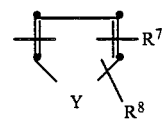

in which Y is oxygen, sulfur, $-CH=CH-$, $-NR^9-$ or $-CR^{10}=N-$, $R^7$ is hydrogen, halogen, $C_1-C_3$-alkyl, $C_1-C_3$-alkoxy, nitro or trifluoromethyl, $R^8$ is hydrogen, halogen, $C_1-C_3$-alkyl, $C_1-C_3$-alkoxy, nitro, $-C\equiv CH$, or one of the groups

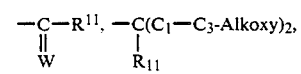

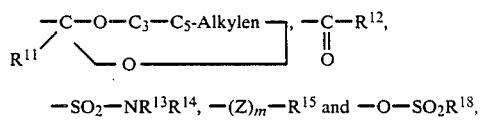

$R^9$ and $R^{10}$ independently of one another are hydrogen, $C_1-C_3$-alkyl or $C_2-C_4$-alkenyl, $R^{11}$ is hydrogen, $C_1-C_3$-alkyl, $C_1-C_3$-halogenoalkyl, $C_3-C_6$-cycloalkyl or $C_2-C_4$-alkoxyalkyl, $R^{12}$ is $C_1-C_6$-alkoxy, $C_3-C_6$-alkenyloxy, $C_3-C_6$-alkinyloxy, $C_2-C_6$-halogenoalkoxy, $C_1-C_4$-cyanoalkoxy, $C_1-C_6$-alkylthio, $C_3-C_6$-alkenylthio, $C_3-C_6$-alkinylthio, $C_5-C_6$-cycloalkoxy, $C_2-C_6$-alkoxyalkoxy or $-NR^{16}R^{17}$, $R^{13}$ is hydrogen, $C_1-C_3$- alkyl or $C_3$-$C_4$-alkenyl, $R^{14}$ is hydrogen, $C_1$-$C_3$-alkyl, $C_1$-$C_3$-cyanoalkyl or $C_1$-$C_3$-alkoxy, $R^{15}$ is $C_3$-$C_6$-alkinyl, $C_2$-$C_6$-alkenyl, $C_1$-$C_6$-alkyl, $C_1$-$C_4$-halogenoalkyl, $C_2$-$C_4$-halogenoalkenyl or $C_1$-$C_4$-alkyl, substituted by cyano, methoxy, ethoxy, nitro, $C_1$-$C_4$-alkoxycarbonyl, methylthio, ethylthio, methylsulfonyl or ethylsulfonyl; or $C_3$-$C_4$-alkenyl substituted by nitro, cyano, methoxy or ethoxy, $R^{16}$ is hydrogen, $C_1$-$C_3$-alkyl or $C_3$-$C_4$-alkenyl, $R^{17}$ is hydrogen, $C_1$-$C_3$-alkyl, $C_1$-$C_3$-cyanoalkyl or $C_1$-$C_3$-alkoxy, $R^{18}$ is $C_1$-$C_3$-alkyl and $C_1$-$C_3$-halogenoalkyl, W is oxygen or sulfur, Z is oxygen, sulfur, —SO— or —SO$_2$— and m is the number zero or one, or a salt of one of these compounds 2. A compound according to claim 1, in which X is oxygen.

3. A compound according to claim 1, in which A is a group of the formula

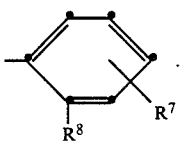

4. A compound according to claim 3, in which $R^7$ is hydrogen and $R^8$ is methoxycarbonyl, ethoxycarbonyl, dimethylaminosulfonyl, propoxy, ethoxy, difluoromethoxy, trifluoromethyl, chloroethoxy, methoxyethoxy, 2,2,2-trifluoroethoxy, 1,2-dichlorovinyloxy, nitro, fluorine, chlorine, bromine, methyl, methylthio, difluoromethylthio, chloroethylthio, —O—SO$_2$CH$_3$, allyloxy or methoxy.

5. A compound according to claim 1, in which $R^3$ is hydrogen.

6. A compound according to claim 1, in which $R^1$ is methyl or ethyl, $R^2$ is methoxy or methyl and E is the group =CR$^4$—.

7. A compound according to claim 6, in which $R^4$ is chlorine, bromine, methoxy, ethoxy, methyl, ethyl, methylthio, dimethylamino, trifluoromethyl or 2,2,2-trifluoroethoxy.

8. A compound according to claim 1, in which $R^1$ is methyl or ethyl, $R^2$ is methoxy or methyl, $R^3$ is hydrogen, X is oxygen, A is the group

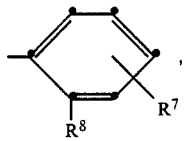

$R^7$ is hydrogen, $R^8$ is methoxycarbonyl, ethoxycarbonyl, dimethylaminosulfonyl, methoxy, ethoxy, difluoromethoxy, trifluoromethyl, chloroethoxy, methoxyethoxy, 2,2,2-trifluoroethoxy, 1,2-dichlorovinyloxy, nitro, fluorine, chlorine, bromine, methyl, methylthio, difluoromethylthio, chloroethylthio, —O—SO$_2$CH$_3$ or allyloxy, E is the group =CR$^4$— and $R^4$ is chlorine, bromine, methoxy, ethoxy, methyl, ethyl, methylthio, dimethylamino, trifluoromethyl or 2,2,2-trifluoroethoxy.

9. A herbicidal and plant growth-inhibiting composition, which contains, in addition to carriers and/or other additives, at least one substituted sulfonylurea of the formula I, claim 1, as the active substance.

10. A method of controlling undesirable plant growth, which comprises applying an effective amount of an active substance of the formula I according to claim 1 or of a composition containing this active substance to the plants or their environment.

11. A method of inhibiting plant growth, which comprises applying an effective amount of an active substance of the formula I according to claim 1 or of a composition containing this active substance to the plants or their environment.

12. A method of influencing plant growth for the purpose of increasing yield, which comprises applying an effective amount of an active substance of the formula I according to claim 1 or of a composition containing this active substance to the plants or their environment.

13. A method according to claim 10 for selective pre- or post-emergent control of weeds in crops of useful plants.

14. A method according to claim 10 for suppressing plant growth beyond the 2-leaf stage, wherein the active substance is applied by a pre-emergent method.

15. 3-[3-(2-methoxycarbonylphenylsulfonyl)-ureido]-1,5,6-trimethylpyrazin-2-one.

16. 3-[3-(2-methoxycarbonylphenylsulfonyl)-ureido]-1,6-dimethylpyrazin-2-one

* * * * *